United States Patent [19]

Cramer, III et al.

[11] Patent Number: 5,025,388

[45] Date of Patent: Jun. 18, 1991

[54] COMPARATIVE MOLECULAR FIELD ANALYSIS (COMFA)

[76] Inventors: Richard D. Cramer, III, 4100 Laclede Avenue, #314, St. Louis, Mo. 63108; Svante B. Wold, 3326A Gullsj',acu/o/ , S-9110, Vánnás, Sweden

[21] Appl. No.: 237,491

[22] Filed: Aug. 26, 1988

[51] Int. Cl.⁵ ............................................. G06F 13/46
[52] U.S. Cl. ..................................... 364/496; 364/578
[58] Field of Search ................ 364/496, 497, 499, 578, 364/577, 300, 200, 900; 436/86, 89

[56] References Cited

U.S. PATENT DOCUMENTS

| | | | |
|---|---|---|---|
| 4,473,890 | 9/1984 | Araki | 364/900 |
| 4,642,762 | 2/1987 | Fisanick | 364/300 |
| 4,704,692 | 11/1987 | Ladner | 364/496 |

Primary Examiner—Parshotam S. Lall
Assistant Examiner—Ellis B. Ramirez
Attorney, Agent, or Firm—Robert B. Famiglio; Robert S. Lipton; Laurence A. Weinberger

[57] ABSTRACT

Comparative Molecular Field Analysis (CoMFA) is an effective computer implemented methodology of 3D-QSAR employing both interactive graphics and statistical techniques for correlating shapes of molecules with their observed biological properties. For each molecule of a series of known substrates the steric and electrostatic interaction energies with a test probe atom are calculated at spatial coordinates around the molecule. Subsequent analysis of the data table by a partial least squares (PLS) cross-validation technique yields a set of coefficients which reflect the relative contribution of the shape elements of the molecular series to differences in biological activities. Display in three dimensions in an interactive graphics environment of the spatial volumes highly associated with biological activity, and comparison with molecular structures yields an understanding of intermolecular associations. CoMFA will also predict the biological activity of new molecular species.

93 Claims, 5 Drawing Sheets

COMPARATIVE MOLECULAR FIELD ANALYSIS (COMFA)

BACKGROUND OF THE INVENTION

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

1. Field of the Invention

This invention relates to the method of comparing in three dimensions the steric and electrostatic fields exerted by molecules with similar binding affinities for a common molecule, and extracting by cross correlation of the fields, the most important common topological features related to the observed differences in binding affinities among those molecules. This method is particularly useful in understanding structure/function relationships in biological chemistry.

2. Description of Related Art

During the past three decades modern biology has come to recognize the importance of the three-dimensional conformation/shape of biological molecules in relation to the observed function and activity of these molecules. Beginning with the first identification of alpha helical structures in proteins through the solution to the structure of DNA as a hydrogen bonded intertwined double helix to current studies by X-ray crystallography of enzyme-substrate complexes, appreciation of the role of shape as a determining factor has continually increased. In fact, it is now understood that a proper description and understanding of the functioning of most biological macromolecules is dependent on an understanding of the three-dimensional shape of the molecules. The situation is often analogized to that of a three-dimensional jigsaw puzzle, where the parts which must fit together interlock in specific patterns in three dimensions. It is now realized that the binding of a molecular substrate to an enzyme is determined by the ability of the substrate to fit a notch/groove/cavity within the enzyme in such a manner that the substrate is both mechanically and chemically stabilized in the correct three-dimensional and thermodynamic orientation to promote the catalytic reaction. Similarly, it has long been recognized that the highly specific binding of antibodies to antigens is accomplished by the recognition by the antibody of the surface shape specific features of the antigen molecule.

Not only is the understanding of these three-dimensional puzzles important to a fundamental understanding of enzymology immunology, and biochemistry, but such studies are of major interest to therapeutic drug researchers. Most drug effects are accomplished by the binding of a drug to a target receptor molecule. To the extent that the nature of the binding is more fully understood, it should be possible to design drugs which bind to their target molecules with greater precision and effect than even naturally occurring compounds. This therapeutic quest is especially important in cancer research where the generalized side effects of many therapeutic drugs are undesirable and more specific drug interactions are desired.

Along with the recognition of the importance of the three-dimensional stereo conformation of biomolecules has come an appreciation of just how difficult it is to understand how the conformation of the molecules is related to their activity. At the present time, the only known method for determining exactly the three-dimensional shape of any biomolecule is by means of X-ray crystallography. While the number of biomolecules which have had their structure successfully determined by crystallography is growing rapidly, the total number remains relatively small, and an even fewer number have been studied in crystal form in conjunction with their bound substrates or ligands. Of the few ligand-biomolecule combinations which have been successfully analyzed by X-ray crystallography, there is still the open question as to whether the complex exists in a different conformational combination in solution than it does in the crystallized form used for the study, although the evidence suggests that there is no major difference.

The study of the three-dimensional conformation/shape of molecules is thus seen to be one of the core questions in modern molecular biology and biophysics. With the possible exception of the introduction in the not too far distant future of coherent X-ray lasers which may make the three-dimensional imaging of biological macromolecules considerably easier, there have been no fundamental advances in the instrumental techniques available during the last several years. Nor have recent advances in protein sequence determination, either by direct sequencing of the proteins or by sequencing of the precursor DNA molecules, been of much help in elucidating the three-dimensional structures since it was discovered early on that, due to the highly folded protein structure, amino acid side chains from vastly different sections of a protein are involved in the conformation of the receptor or binding site. Similar considerations are true with respect to antibody formation. Only recently has a proposal been made towards understanding the initiation of alpha helixes, perhaps the simplest tertiary protein structure, based on a knowledge of the amino acid sequence in a protein. See Presta, L. G.; Rose, G. D. Science 1988, 240, 1632.

Recognizing the difficult and lengthy time involved in obtaining X-ray crystallographic structures of biomolecules, researchers have pursued alternate, though less exact, paths towards obtaining information on the stereochemical binding of molecules. One such approach, taken by experimental chemists, has been to apply an understanding of basic chemical principles to analyze the likely binding sites of substrates. By examining the chemical structures of various ligands known to bind to a given protein, and relying on an understanding of generalized chemical and stereochemical principles, chemists have made educated guesses concerning which parts of the substrate/ligand would most likely be involved in binding to the protein. Based on these educated guesses, new compounds have been synthesized incorporating predicted reactive sites. The binding affinities of the new substrates for the desired protein have been measured. Some reasonable measure of success in understanding stereochemical binding has been achieved by this empirical method, but failure has been much more frequent than success. This scheme, though rational, is basically one of trial and error and does not lead to a coherent approach to finding or designing new molecules with the desired binding affinities.

Attempts have been made over the years to place the understanding of stereochemical interactions of biomolecules and the development of new substrate molecules on a more quantitative footing. These approaches attempt to systematically relate differences in structures of similar substrate molecules to differences in their observed biological activities. Thus, a "structure activity relationship" (acronymed SAR) is sought for a given class of substrates/ligands. To the extent that these approaches have now been quantified, they are now referred to as "quantitative structure activity relationships" (acronymed QSAR). Generally, the relationship sought in formulating a QSAR is cast in the simplest possible format, that of a linear combination of elements. Thus the measured biological value, V, is sought to be explained by a series of terms, A, B, C, etc. as the linear combination: $V=A+B+C+\ldots$ The QSAR approach can be used to relate many measures/properties of molecules which are somehow reflective of their structure, such as partition coefficients and molar refractivity. In the past these indirect measures of shape have been used in QSAR studies since using direct measures of shape proved conceptually and computationally difficult. As the art has progressed, and as the structural differences used in QSAR studies have become primarily molecular shape differences, the field of "three-dimensional quantitative structure activity relationships" (acronymed 3D-QSAR) has evolved.

The 3D-QSAR approach quantifies chosen shape parameters and tests to see if a correlation can be found between those parameters and a biological variable, typically binding affinity. It has turned out to be a very complex problem to model the interaction between a ligand and its receptor. The principal difficulty has been finding a quantitative way in which to express the simple concept of shape. As is often the case, what is visually obvious to the human eye and brain is complex to describe quantitatively or mathematically. While describing shape is difficult enough, searching for similarities in shape using shape descriptors which are, at best, inadequate turns out to be exceedingly difficult.

The general approach used in the QSAR methodology relies on the fact that, for most proteins, there are a number of chemical compounds or substrates having known structural differences which bind with differing affinities to the protein. The rationale behind the 3D-QSAR approach is that it should be possible to derive shape descriptors which, when applied to the various substrates, will reflect the different binding affinities. In 3D-QSAR a similar underlying assumption is made as in other QSAR approaches, i.e., that the relevant biological parameter, usually a binding affinity, can be represented as a linear combination of weighted contributions of the various shape descriptors for the substrate molecules. Once a whole series of substrates are described with the same shape descriptors, it should be possible to compare or correlate the shape descriptors and extract the critical shape determinants found to be associated with the differences in biological activity amongst the substrates.

From a knowledge of the most significant structural shape elements of the substrate or ligand, one could then infer the important elements of the receptor site on the protein. Ideally, in this process one would have at least as many substrates to compare as one had variables among the shape descriptors. Thus, a system of equations with the number of equations equaling the number of shape descriptors with unknown weighting coefficients would exist and could be solved exactly. However, in practice, it quickly became evident that, even with simplifying assumptions, using available shape descriptors to describe the properties of an unknown shape, the number of descriptor variables far exceeds the number of available substrates for which binding data is known. Thus, rather than getting an exact solution, it was found that approximating statistical methods had to be used to extract from the numerical shape descriptors the shape elements which best correlated with observed biological activity. However, until very recently statistical methods were not available which could extract useful information from a system of equations containing many more variables than equations.

During the past decade work has progressed in this field. From chemical analysis of substrate-protein complexes, it is known that the molecular interactions that produce an observed biological effect are usually non-covalent. Thus, the forces important for intermolecular association are believed to arise from hydrophobic, van der Waals (steric), hydrogen bonding, and electrostatic interactions. Attempts have been made to build shape descriptors based on these properties, but, unfortunately, the immense number of degrees of freedom and large labile protein-substrate complexes make the mathematical modeling of the shape of the complexes extremely difficult. Further simplifying criteria and assumptions were found to be necessary.

One such approach, entitled the Molecular Shape Approach developed independently by Simon, et al. (see Simon, Z; Badilenscu, I.; Racovitan, T. J. Theor. Biol. 1977, 66, 485 and Simon, Z.; Dragomir, N.; Planchithin, M. G.; Holban, S.; Glatt, H.; Kerek, F. Eur. J. Med. Chem. 1980, 15, 521) and Hopfinger, (see Hopfinger, A. J. J. Am. Chem. Soc. 1980, 102, 7196) compares net rather than location-dependent differences between molecules. That is, a shape characteristic of the total molecule is calculated in which the details of specific surface characteristics are merged into an overall molecular measure. The most active molecule in a series (in the sense of biological affinity) is considered to be a template molecule which has an optimal fit to the receptor site in the protein. Differences in activity amongst the series of substrate molecules are, therefore, potentially correlated by a multiple regression analysis with three structure (or shape) parameters definable for each member of the series. The shape parameters initially considered were either: 1) the common volume, 2) the volume possessed by the most active molecule, but not by the less active molecule, and 3) the volume possessed by the less active but not by the most active molecule in the series. Hopfinger describes these parameters as Common Overlap Steric Volumes and interprets them as quantitative measures of relative shape similarity.

More recently Hopfinger (see Hopfinger, A. J. J. Med. Chem. 1983, 26, 990) has constructed a new set of molecular shape descriptors derived from the potential energy field of a molecule. In this approach, Hopfinger uses molecular mechanics potentials as a means of estimating the molecular potential energy fields:

$$P_u(R,\theta,\phi) = \sum_{i=1}^{n} \left[ \frac{a(T)_i}{r_i^6} + \frac{b(T)_i}{r_i^{12}} + \frac{Q_i Q(T)}{\epsilon(r_i)(r_i)} \right]$$

In this equation the molecular potential energy field $P_u(R,\theta,\phi)$ at any given point $(R,\theta,\phi)$ for molecule u is defined; $a(T)_i$ and $b(T)_i$ are the attractive and repulsive potential energy coefficients, respectively, of atom i of molecule u interacting with the test probe T which is treated as a single force center; $Q_i$ and $Q(T)$ are, respectively, the charge densities of the ith atom and the test probe; $\epsilon(r_i)$ is the dielectric term; n is the number of atoms in u, and $(r_i)$ is the distance between atom i and the test probe. Hopfinger suggests that pairwise field-difference $[\Delta P_u]$ descriptors may correlate with biological parameters in a 3D-QSAR. Note, however, that this is a net molecular shape descriptor rather than a specific location-dependent shape descriptor.

A second approach is the Distance Geometry Method of Crippen. See for example Ghose, A.; Crippen, G. J. Med. Chem. 1985, 28, 333. In this approach the user must provide a "pharmacophore" or a list of potential receptor-binding atoms on each of the substrates/ligands having specified physicochemical properties. Knowledge of the pharmacophore comes from chemical studies of the binding properties of the given series of substrate molecules. The user must also provide a "binding site", a set of points in Cartesian space which are capable of interacting with a nearby pharmacophore atom, the magnitude of the attraction or repulsion depending on the nature of the atom. The geometrically allowed interactions between the ligand atoms and the binding site are determined. Each ligand is free to move or experience torsional deformations, in any fashion that minimizes the sum of its site points' energies of interaction with the "binding site". Thus, following Crippen, who again assumes a linear function for the interaction, the binding energy of a particular binding mode will be given by:

$$E_{CALCD} = -C E_c + \sum_{i=1}^{n_s} \sum_{j=1}^{n_p} \left[ C'_{i'j} \sum_{k=1}^{n_o} P_j(t_k) \right]$$

where $E_c$ is the energy of the conformation; C's are the coefficients to be determined by quadratic programming; i' is the type of site i; $n_s$ represents the number of site pockets; $n_p$ represents the number of parameters to correlate with that site pocket interaction; $n_o$ represents the number of atoms occupying that site pocket; $P_j$ represents the jth physiochemical parameter of the atom of type $t_k$.

A successful 3D-QSAR is found when the sum of the energies of interaction obtained is suitably close to the binding affinities observed experimentally. The result provides both a receptor map (the position and nature of the "binding site" points) and, for each member of the series, an active conformation of that molecule. In both the Hopfinger and Crippen approach, it will be noted that an initial educated guess must be made for the choice of the active conformation of the molecule before the analysis can be done, and Crippen must further hypothesize an actual receptor site map in three dimensions.

Another major problem in any quantitative approach to shape analysis is the fact that, in solution, most compounds exist as a mixture of rapidly interequilibrating shapes or conformers. Generally, it is not even known which of the multiple conformations of a molecule is responsible for its measured biological affinity. Once again, educated guesses must be made to decide which of the many molecular conformations will be used in a 3D-QSAR analysis. The existence of multiple conformations further complicates the task of choosing the correct molecular orientation in which to make the comparison between the substrate molecules. Obviously, the ability of any shape measure to compare molecular shapes relies upon the correct relative orientation of the molecules when the shape measure is first determined. The same molecule when compared to itself rotated by 90° would not likely show any common structural features. Therefore, several of the 3D-QSAR methods rely upon alignment rules to guarantee that only the variable or differing parts of the molecules make the greatest contribution to the shape comparison. It is obvious that the existence of multiple conformations for a given molecule complicates this task.

Typically then, a 3D-QSAR analysis starts out with many shape dependent parameters for a relatively few molecules whose biological activity, such as binding affinity, is known. This results in a series of linear relationships/equations relating the shape parameters to the biological measures having many more unknowns (columns) than relationships (rows). Except in the limiting cases of shape descriptors where oversimplifying assumptions are made, no statistical regression or correlation methods were available until recently which could give any possible hope of solving such a set of equations.

BRIEF SUMMARY OF THE INVENTION

The present invention is an effective computer methodology employing both interactive graphics and statistical techniques for correlating shapes of molecules with their biological properties. The method of the present invention utilizes a new approach to 3D-QSAR which provides an objective and quantitative measure of the three-dimensional shape characteristics of all areas of a molecule and, at the same time, requires very few limiting assumptions. The quantitative description of the shape of the molecule is derived from an analysis of the steric and electrostatic interactions of the atoms comprising the molecule with a test probe. The resulting interaction energies calculated at all intersections in a three-dimensional grid or lattice surrounding the molecule form the quantitative shape descriptors entered along with the molecule's measured biological activity as a row in a data table.

Each molecular conformation may be similarly described as a row of lattice point energies associated with the same measured biological activity. Selection of the conformers of choice can be made on either an empirical basis or by a weighted average, typically a Boltzman distribution of the various conformations. A row of interaction energies representative of the conformations of a given molecule is then used. The resulting 3D-QSAR table typically has several thousand columns of lattice point energies and a number of rows corresponding to the number of molecules in the series being investigated.

Theoretically, a complete description of the shape differences between the molecules under a study is contained in this table, but previously no statistical methodology was available to extract useful information from the table. Unless either limiting assumptions about binding sites are made which reduce the number of columns, or knowledge exists about the specific binding sites of a specific conformation, an infinite number of sets of coefficients can be calculated which would yield the same biological parameter values. Early in the 1980's a statistical methodology was derived which explicitly solves this type of multivariate problem. This methodology is called Partial Least Squares Analysis (PLS).

The software of the present invention permits four different alternative procedures to be used to align the molecules in the three-dimensional lattice. They are: 1) a user specified alignment based on other data; 2) the Fit routine; 3) the Orient routine; and, finally, 4) the Field Fit procedure which minimizes the differences in the calculated fields of the atoms between the various molecules. Preferably the alignment will be done by Field Fit. A 3D-QSAR table is generated and then analyzed according to the PLS method as modified for CoMFA. Resulting solution of the 3D-QSAR table yields coefficients of the column terms which represent the relative contributions of the various lattice positions to the biological activity. Since the solution is re-expressed in terms of interaction energy values similar to those that were calculated in creating the 3D-QSAR table, it is possible to reverse the process and display on a video terminal a plot of the interaction energies to reveal those areas of molecular shape associated with differences in biological activity. In an interactive graphics display environment, the invention allows the user to vary the analytical options and, in a reasonable time frame, see the areas of molecular shape most important to biological activity highlighted on the screen in front of him. By a study of the changing display as the parameters are varied, the user may obtain an understanding of how particular shape characteristics of the molecule are important to its biological activity.

It is a purpose of the present invention to compare the shapes of molecules with shape descriptors highly sensitive to local surface area differences. In addition, it is a purpose of the present invention to provide a methodology for making a quantitative estimate of the importance of the various components of molecular shape to the biological activity of a molecule. A further purpose of the present invention is to provide structural, conformational, and statistical information which will allow users to suggest or identify new molecules which might be used as substrates/ligands. Finally, it is a purpose of the present invention to provide an interactive graphics environment in which the various parameters of shape can be studied in a quantitative fashion in order to obtain a more thorough knowledge of the nature of intermolecular interactions.

DETAILED DESCRIPTION OF THE INVENTION

The present invention overcomes the limitations of earlier 3D-QSAR approaches and allows significant insights int molecular interactions never before achieved without actual X-ray crystallographic knowledge of the receptor binding sites. In fact, to the extent X-ray results provide only a static picture, the present invention provides more detailed knowledge of the shape differences operative in dynamic interactions between molecules in solution. The Comparative Molecular Field Approach (CoMFA) is a heuristic procedure for defining, manipulating, and displaying the differences in molecular fields surrounding molecules which are responsible for observed differences in the molecules' activities. This description of CoMFA is arranged in three progressively more detailed sections: first, an overview of the entire process; second, descriptions of the individual components including a rationale for each component and the differences with the prior art; and third, annotated software source code implementing CoMFA.

CoMFA OVERVIEW

Once a series of molecules, for which the same biological interaction parameter has been measured, is chosen for analysis, the three-dimensional structure for each molecule is obtained, typically from the Cambridge Crystallographic Database or by standard molecular modeling techniques. The three-dimensional structure for the first molecule is placed within a three-dimensional lattice so that the positional relationship of each atom of the molecule to a lattice intersection (grid point) is known. A probe atom is chosen, placed successively at each lattice intersection, and the steric and electrostatic interaction energies between the probe atom and the molecule calculated for all lattice intersections. These calculated energies form a row in a conformer data table associated with that molecule.

Interaction energies for additional conformations of the first molecule may be similarly calculated. After each row of interaction energies is calculated for each conformer, the conformer is aligned by a field fit procedure which minimizes the energy differences at each lattice point between that conformer and the first conformer. The field fit interaction energy values for each conformer are then entered into the data table for the first molecule. Once the interaction energies for all conformations of the first molecule have been calculated, an averaged value of the interaction energies at each lattice point of all the conformers becomes the first row in a 3D-QSAR data table associated with the measured biological parameter for the first molecule.

Figure 1:
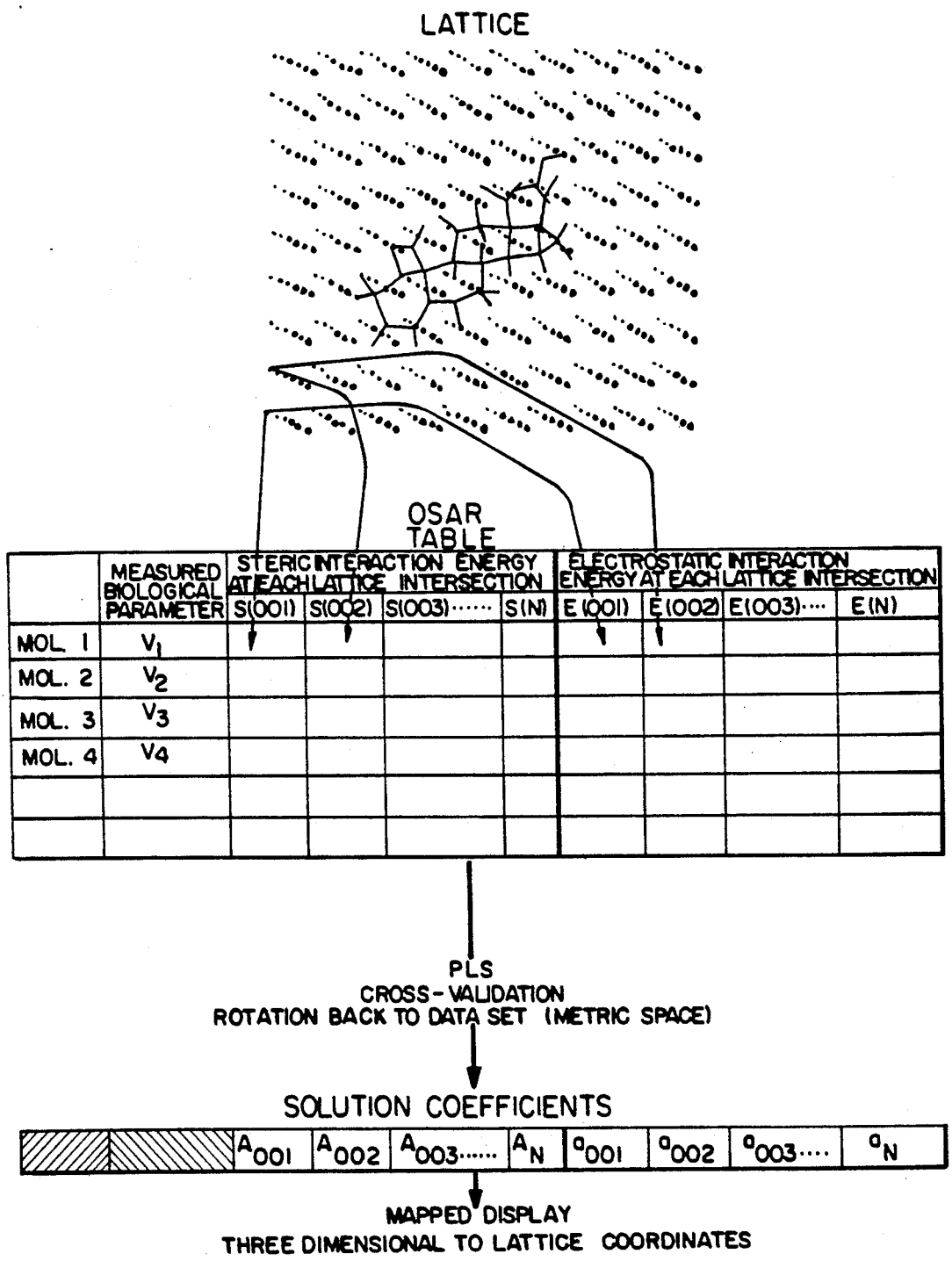
FIG. 1 is a schematic illustration and overview of the CoMFA method.

An identical procedure is followed for all the molecules in the series. After the averaged value over the conformations for a particular molecule is entered into the 3D-QSAR table, a field fit minimization of the newly added data to the first molecule aligns the newly added molecule to the others in the series. The upper portion of FIG. 1 diagrammatically shows how the 3D-QSAR table is constructed. For each lattice intersection, the steric or electrostatic interaction energy with a test probe atom placed at the lattice point is entered into the appropriate steric or electrostatic column associated with that point. The intersection points are numbered sequentially, and the corresponding column identified as steric(S) or electrostatic (E).

Once the data (interaction energies and measured biological activity) for all molecules in the series are entered into the 3D-QSAR data table, a Partial Least Squares (PLS) analysis is performed which includes a cross-validation procedure. Using the interaction energies for each lattice position and the biological values, in essence, PLS solves a series of equations with more unknowns than equations As shown in the lower portion of FIG. 1, the resulting solution is a series of coefficients, one for each column, the value of which (in energy units) reflects the contribution of the interaction energies at that lattice position to differences in the measured biological parameters.

Figure 3A:
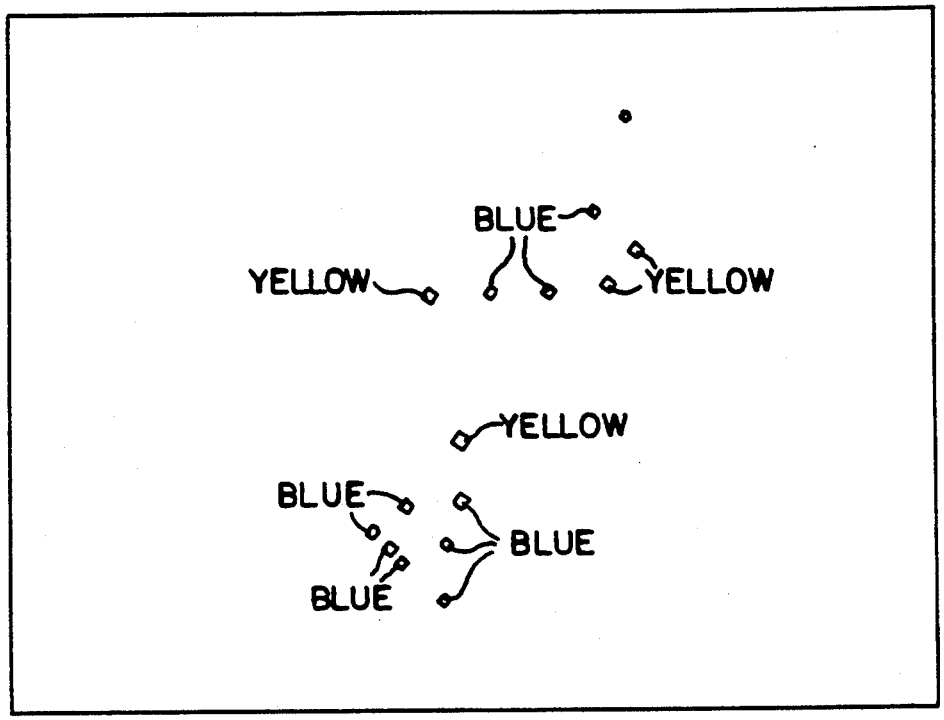
FIG. 3A shows a scatter plot in three-dimensional lattice space of a steric CoMFA solution.
Figure 3B:
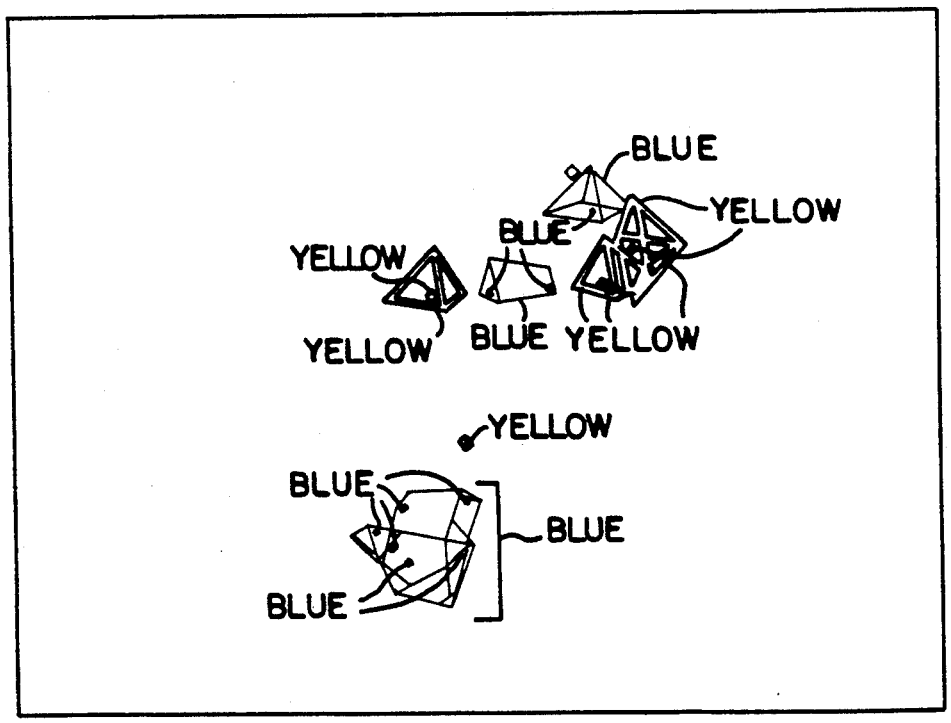
FIG. 3B shows a counter plot in three-dimensional lattice space of the same CoMFA solution shown in FIG. 3A.

While the solution has many terms, the one-to-one correspondence between a term and a lattice point allows the solution to be presented as an interactive color-coded three-dimensional image, either in the form of a graph visually similar to the top part of FIG. 1,(see FIG. 3A) the color of a point signifying the magnitude of the corresponding terms, or better, with term values summarized in contour form (see FIG. 3B). The graphic representation clearly shows the area in molecular space where the 3D-QSAR strongly associates changes in molecular field values with changes in the measured biological parameter.

MOLECULAR FORCE FIELDS

As pointed out above, biochemists and biophysicists have come to believe that intermolecular interactions are highly stereo specific, depending mainly on shape complementarity, and that biological molecules solve a three-dimensional jigsaw puzzle every time they bind. However, the prior art 3D-QSAR shape descriptors mentioned earlier give only a net measure of overall shape, totally averaging out local topological differences between molecules. These methods are actually aggregate indices, which describe a "shape" only to the same extent, for example, that the comparative "shape" of two sculptures is described by measuring their differential weight or volume. Likewise, ball and stick molecular models do not reflect either the steric interactions of extended molecular orbitals or charge associated interactions.

In order to describe molecular shape, a descriptor should be sensitive to at least three molecular parameters: first, it should account for the true steric bulk of each atom in the molecule; second, it should account for electrostatic interactions of each atom in the molecule; and, third, it should be a fine enough measure to reflect every local topological feature of the molecule. The approach used in CoMFA is that a suitable sampling of the steric and electrostatic interactions of a molecule will suffice to answer most questions about its possible shape dependent receptor interactions. The calculation of interaction energies at lattice points surrounding a molecule is not, in itself, new. Others have tried to use this approach as an estimate of molecular shape. For example, Goodford has described the use of probe-interaction "grids" similar to those calculated in the present invention. See Goodford, P. J. J. Med, Chem. 1985, 28, 849.

In theory, the row of interaction energy data generated from all lattice points contains most of the information describing how a molecule "looks" to a receptor in three dimensions. However, before this invention, no one has discovered how to compare the shapes of different molecules represented by these rows of data or to extract and visualize useful information about the shape differences which are important to molecular associations.

The fineness or resolution with which the shape of a molecule is described by this method depends on three factors: 1) the steric size of the test probe atom, 2) the charge on the test probe atom, and 3) the lattice spacing. The software of the invention allows the user to specify both the steric size and charge of the test probe. In addition, the probe parameters may be varied at different lattice locations which the user believes calls for finer or coarser measurements. The user may also select the lattice spacing. Typically probe atom size is varied from that of covalent hydrogen —H, to $sp^3$ carbon, to $sp^3$ oxygen, to divalent sulfur. The probe charges used typically are $+1.0$ and $0.0$, while lattice spacing values of 1.0 to 4.0 angstroms are frequently employed.

Van der Waals radii are generally used for the steric calculation and atomic charges can be calculated from knowledge of atomic coordinates. Thus, the steric interaction energy is calculated as:

$$\sum_{i=1}^{N_{at}} \left[ \frac{A_i}{r_i^{12}} - \frac{B_i}{r_i^6} \right]$$

where $N_{at}$ is the number of atoms in the biomolecule; $r_i$ is the distance between the probe atom and the ith atom in the biomolecule; and $A_i$ and $B_i$ are constants characteristic respectively, of the probe atom type and the type of the ith atom in the biomolecule. [Other values can be selected by the user as an option in place of the exponent 12- see Software Disclosure.] The electrostatic interaction energy is calculated as:

$$\sum_{i=1}^{N_{at}} \frac{Qq_i}{r_i^2}$$

where the $N_{at}$ and $r_i$ are the same as for the steric calculation; $Q$ is the charge on the probe atom; and $q_i$ is the charge on the ith atom. The $q_i$ may be calculated by the method of Gasteiger and Marsili. See Gasteiger, J.; Marsili, M. Tetrahedron 1980, 36, 3219. [The user may omit the exponent 2 as a user option—see Software Disclosure.] Since the probe atom is placed successively at all lattice points, for those points within the molecule the steric repulsion values can become enormous. Since there is no significance to the absolute value other than to estimate how much atomic volume overlap exists, whenever the probe atom experiences a steric repulsion greater than a "cutoff" value (30 Kcal/mole typically), the steric interaction is set to the value "cutoff", and the electrostatic interactions are set to the mean of the other molecules' electrostatic interactions at the same location. These cutoff values may also be selected by the user of the programs. Obviously no topological information is lost.

It should be recognized that any property which can be calculated from a molecular model, such as interatomic distances or torsion angles, can become an additional column in the 3D-QSAR table. Columns may also contain values of other molecular parameters (such as logP or heats of formation), data defined as functions of other columns, or even data that is calculated via custom procedures provided by the user. In addition, since measured biological activity is a consequence both of a molecule's ability to get to the receptor site as well as to bind to the receptor, additional terms (columns) which reflect molecular diffusion may be incorporated. It should be appreciated that the statistical and visual correlation of data in the columns by the methods of the present invention is not limited to interaction energy shape descriptors.

In fact, a most significant and powerful feature of the present invention is that the CoMFA method will yield information not even available from X-ray crystallographic studies since X-ray results present static pictures which are not totally dispositive of the dynamic interactions in solution. By comparison, the CoMFA model of the interaction is phenomenological. The actual measured activity is expressed or predicted in terms of determinable quantities. The present invention will display the dependence of the measured biological parameter on data (shape and other relevant information) contained in all columns.

For development of the present invention, all positioning of Tripos Associates, Inc. References to SYBYL data structures can be seen in the source code. However, there are several other programs available which are functionally equivalent and may be used with the present invention. Examples are:

ChemX—from Chemical Design Ltd., Oxford, UK

Insight—from BioSym Technologies, San Diego, Calif.

Quanta—from Polygen, Waltham, Mass.

ChemLab—from Molecular Design Ltd., San Leandro, Calif.

MacroModel—from Prof. Clark Still, Columbia Univ.

Such a host program must support the building and storage of molecular models (retrieval of the atomic coordinates) plus the calculation of atomic charges (for electrostatic field computation) and the tabulation of steric parameters by atomic type (for steric field computation).

A list of the data structures required by all CoMFA programs is presented as Q3DEF.C and DABDEF.C to facilitate the integration of other programs with CoMFA.

ALIGNMENT AND FIELD FIT

CoMFA works by comparing the interaction energy descriptors of shape and relating changes in shape to differences in measured biological activity. Since the shape descriptors are calculated at each lattice point, the lattice site-specific interaction energies calculated for the same molecule offset by even one lattice point will be significantly different. A CoMFA analysis of this data will show differences in shape where there are none. Therefore, the positioning of a molecular model within the fixed lattice is by far the most important input variable in CoMFA since the relative interaction energies depend strongly on relative molecular positions within the lattice.

The Field Fit feature of the present invention aligns molecules to minimize their field differences rather than atomic coordinate differences. Since the interaction energies reflect molecular shape, they can be quantitatively manipulated for shape alignment. This is a particularly suitable approach since the intermolecular comparisons are based on these same energy fields.

In Field Fit, any molecule may be used as the reference. However, if fitting conformations of the same molecule, the conformation which from other considerations is most likely to be the most active conformer would usually be used as the comparison standard. When Field Fitting the final series of test molecules, the molecule with the greatest biological activity would usually be used as the reference. In the Field Fit alignment, the root means squared (RMS) difference in the sum of steric and electrostatic interaction energies averaged across all lattice points, between the new molecule and the reference molecule or set of molecules, is minimized with respect to the six rigid-body degrees of freedom, any user-specified torsion angles, and any change in internal geometry. The user has the option before Field Fitting of weighting those lattice positions which he believes form other considerations may be particularly significant to the alignment of a given molecular series or conformation. The results of Field Fit alignments or test alignments using weighting factors may be displayed and compared visually as three-dimensional scatter or contour plots in the same manner as discussed later for all graphic output.

With reference to the 3D-QSAR table of FIG. 1, Field Fitting molecule 2 to molecule 1 would correspond to minimizing the sum of squared differences between the values in all but the first column of the first and second rows of the table, by altering the position and/or torsion angles of molecule 2. Field Fit also requires for satisfactory results a steric repulsion beyond the lattice boundary and, when torsion angles are varied, the conventional molecular mechanics internal energy calculated using the same force field. The reason for the boundary steric repulsion is as follows. The function being minimized can be visualized as being similar in shape to the cross-section of a volcano. The steric boundary repulsion is needed because the answer sought in the minimization is the crater, but if the molecules are not nearly aligned or field-fit to begin with, the down-hill (minimization) direction will be down the outside of the volcano: that is, minimization of the difference in fields will push the molecules apart. By placing steric repulsion at the edge of the lattice region, the down-hill direction along the outside of the volcano will be disfavored.

Field Fit also allows the user to address the relative weighting of the three different contributions to the function being minimized, namely; the field difference itself, the edge steric repulsion, and the differing internal energies as torsional bonds and other internal geometries are altered. The weighting choice is a user option in the program. The Field Fit ability to see in an interactive graphics environment the three-dimensional consequences of various weighting choices on molecular alignment is in itself a significant advance in 3D-QSAR. Minimization is performed by the Simplex method (a widely available algorithm), with step sizes such that individual atoms initially move no more than 0.2 Angstroms. The Simplex method is preferred because the function being minimized does not have analytical derivatives. Convergence occurs when successive function evaluations vary less than 1%. As with any minimization, Field Fit will find a best alignment if the final geometry is expected to closely resemble (be "down-hill" from) the starting geometry.

The CoMFA programs allow other alignment procedures to be followed, such as the standard Fit and Orient routines. For instance, Fit utilizes least squares superposition of user specified sets of nuclei of atoms, with or without relaxation of internal geometry, while Orient takes three user specified atoms and places the first atom at the origin, the second atom along the x axis, and the third atom in the xz plane. The user may even attempt trial and error alignment based on an educated guess or other 3D-QSAR data. Field Fit is particularly useful when a CoMFA based upon some other alignment method gets too low a cross-validated r², caused in turn by one or more molecules having very large residuals (a very large difference between predicted and actual properties in the cross-validation step). A Field Fit of the compound(s) with very large residuals should produce a new alignment which will lead to improvement when the CoMFA is repeated.

The Field Fit procedure also has important applications when used to maximize rather than minimize field differences. If the differences in the interaction energies of two shape complementary molecules are maximized, Field Fit will produce the best three-dimensional alignment or "docking" between the molecules. Thus, if the structures of both the substrate and enzyme (or antigen and antibody) are known, Field Fit will find their optimal alignment.

CONFORMATION SELECTION

A major unsolved problem in prior art approaches to 3D-QSAR is the determination of the proper molecular conformation to use in an analysis. Absent any direct knowledge of the actual active conformation responsible for biological activity, previously the only approach has been to make an educated guess. CoMFA, using Field Fit, allows a quantitative approach to conformation selection. It is possible using the CoMFA Programs to enter into a separate data table the interaction energies of every conformer and fit it to a selected template conformer. Various averaging or weighting schemes can then be employed as user options to determine a most representative conformer. The interaction energies for the various conformations can be weighted based on reasonable assumptions about the likelihood of certain conformations being most active without totally excluding contributions from presumably less active forms. In the alternative, since most conformations are believed to be equilibrated in free aqueous solution at normal temperatures, the CoMFA programs permit the weighting to reflect a Boltzman distribution over the energy of the conformers. Only in the case of a highly labile molecule (one possessing multiple rotomers and tautomers) would a Boltzman distribution produce a fuzzy, averaged, and meaningless ball. CoMFA with Field Fit provides the ability to use these various weighting functions to determine a form of the molecule which the receptor site is most "likely" to see.

PLS—PARTIAL LEAST SQUARES ANALYSIS

As mentioned earlier, the inherently underdetermined nature of a 3D-QSAR table with many more columns than rows has previously posed an insolvable problem which prohibited use as a shape descriptor of the interaction energies calculated at thousands of lattice points. The values in the data table can be viewed as a system of equations with many more unknowns than equations. For instance, for three molecules the following three equations can be written:

$$Value_1 = b^1 + A_{001}S^1(001) + A_{002}S^1(002) + \ldots A_N S^1(N) +$$
$$a_{001}E^1(001) + a_{002}E^1(002) + \ldots a_N E^1(N)$$
$$Value_2 = b^2 + A_{001}S^2(001) + A_{002}S^2(002) + \ldots A_N S^2(N) +$$

-continued
$$a_{001}E^2(001) + a_{002}E^2(002) + \ldots a_N E^2(N)$$
$$Value_3 = b^3 + A_{001}S^3(001) + A_{002}S^3(002) + \ldots A_N S^3(N) +$$
$$a_{001}E^3(001) + a_{002}E^3(002) + \ldots a_N E^3(N)$$

where the Values are the measured biological activities for each molecule; $b^x$ is the intercept for each equation for molecule x; $A_{\_\_}$ and $a_{\_\_}$ are the coefficients of the steric and electrostatic terms which reflect the relative contribution of each spatial location, the subscripts indicating both different coefficient values and the lattice positions with which the values are associated; $S^x(N)$ and $E^x(N)$ are the steric and electrostatic interaction energies calculated at lattice position N (where N ranges from 1 to the maximum number of lattice intersection points) for molecule x. The partial least squares (PLS) method of multivariate analysis "solves" this apparently underdetermined system of equations by a series of orthogonal rotations in hyperspace of both the independent and dependent variable matrices, in each rotation maximizing the commonality between the independent and dependent variable matrix. (In contrast, classical least-squares regression rotates the independent variable columns individually and independently, rather than together, thus consuming a degree of freedom for each coefficient estimated.) The solution to the equations found by PLS is the set of values of the coefficients which come closest to making each equation true. PLS is particularly attractive for CoMFA since it involves only two vector-matrix multiplications, can perform the calculation on raw data, and can solve large problems on a smaller computer.

An important improvement of PLS for use in CoMFA has been created in which the initial PLS solution is rotated back into the original data space thereby re-expressing the term coefficients obtained as the solution in terms of the original metric space (in this case, energy values). Since this solution contains a potentially non-zero coefficient for each column in the data table, (in fact two for each lattice point), it can therefore be displayed and contoured in three-dimensional space, just like any other expression associating numerical values with known locations in space.

Integral to finding a "solution" by PLS is a cyclic cross-validation procedure. Cross-validation evaluates a model not by how well it fits data, but by how well it predicts data. While useful in many situations, cross-validation is critical for validating the underdetermined CoMFA 3D-QSAR tables. A statistical measure of the reliability of the PLS solution is calculated by defining a cross-validated (or predictive) r² analogously to the definition of a conventional r² as follows:

$$\text{cross-validated } r^2 = \frac{SD - \text{Press}}{SD}$$

where SD is the sum over all molecules of squared deviations of each biological parameter from the mean and PRESS (predictive sum of squares) is the sum over all molecules of the squared differences between the actual and predicted biological parameters. A negative cross-validated r² will arise whenever PRESS is larger than SD, that is, whenever the biological parameters are better estimated by the mean of all measured values than by the solution under consideration.

Figure 2:
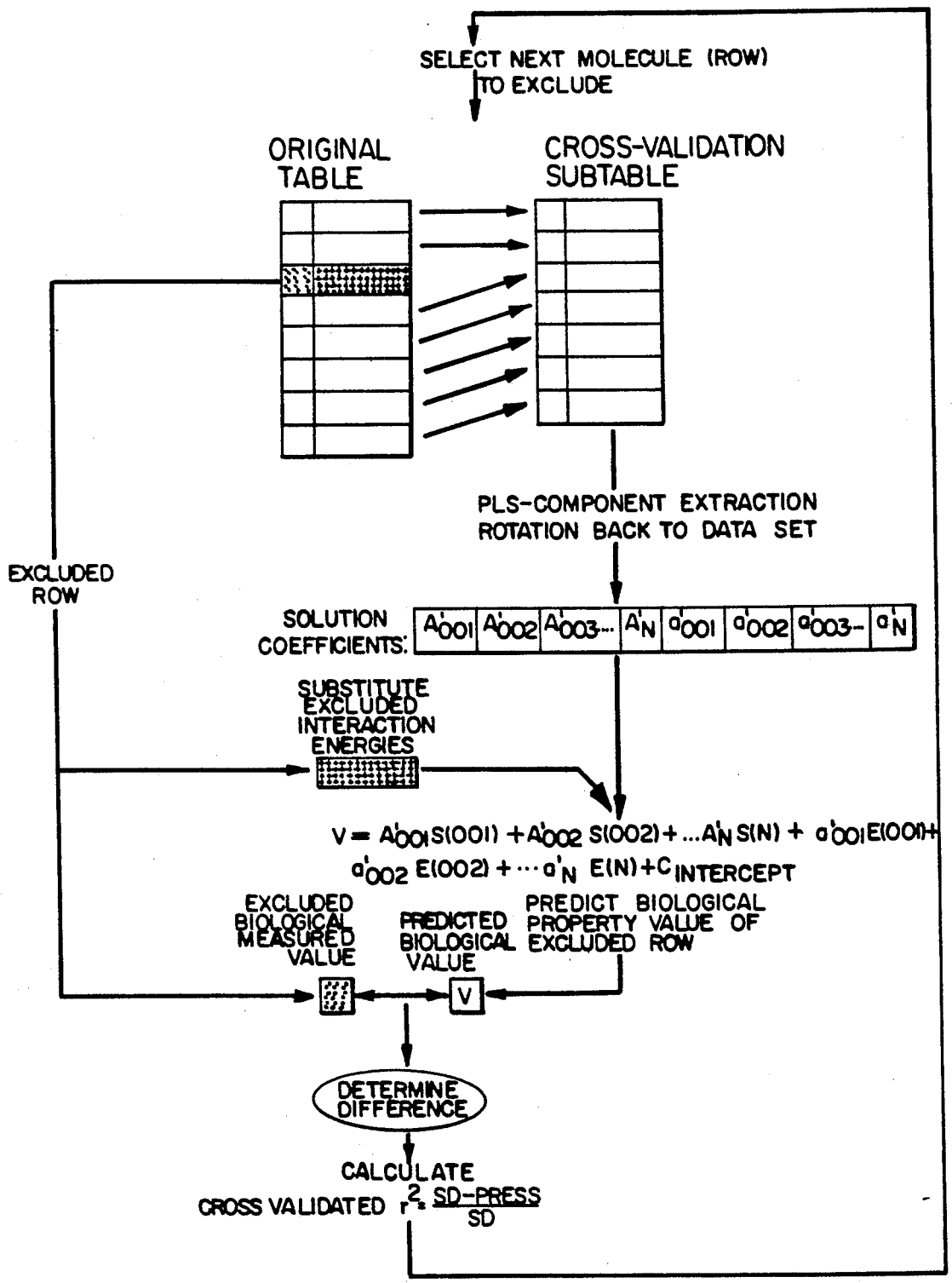
FIG. 2 is a schematic illustration of the cross-validation procedure.

The cross-validation procedure is integrated with PLS as follows. First the entire 3D-QSAR data table is analyzed by PLS and one component extracted in hyperspace. [The projection of this component onto all the orthogonal planes in hyperspace yields components on all the planes which are the equation coefficients sought.] A value of $R^2$ is calculated. The PLS analysis is then repeated (the equation coefficients rederived) with a randomly chosen molecule (row) excluded. The resulting coefficients are used to calculate (predict) the biological value for the excluded molecule (row) and a new $R^2$ is calculated. [In actual practice the program also permits the exclusion of random subsets of molecular values and calculations of the excluded biological values. This reduces the time necessary to compute a first set of coefficients. In a full detailed analysis, each molecule (row) is individually excluded.] This omission, rederivation, and prediction procedure is repeated until every biological parameter value has been predicted by a set of coefficients from whose derivation it was excluded. FIG. 2 shows a schematic outline of this cross-validation procedure. Note how the solution coefficients derived by PLS without the excluded row are used with the interaction energy values from the excluded row in the equation to predict the biological value of the excluded molecule.

Values of $R^2$ and PRESS are calculated for each crossvalidation cycle. If there is no correlation amongst the data, the coefficients derived will not give meaningful predicted values and the PRESS will exceed the SD. The $R^2$ values indicate how good the components are that result from the extraction.

Next, the contribution of the first component already obtained is removed from the matrix hyperspace, a second PLS analysis performed, and an additional component extracted. Another cross-validation round is completed, again completing the omission, rederivation, and prediction cycle. The user specifies the number of times the extraction cross-validation procedure is repeated. The extracted components are added, rotated back into the data space, and the resulting coefficients generated.

The outcome of the PLS/cross-validation analysis of the data table is a set of coefficients (one for each column in the data table) which, when used in a linear equation relating column values to measured biological values, best predict the observed biological properties in terms of differences in the energy fields among the molecules in the data set, at every one of the sampled lattice points.

GRAPHIC DISPLAY

The final step in a CoMFA is the display of the analytical results in a manner meaningful to the biochemical researcher. In general, the human eye and brain is much more skillful in recognizing complex patterns within a picture than within a table of numbers. CoMFA outputs are uniquely able to utilize this inherent advantage in graphical presentations since the three-dimensionality of the input data is retained throughout. Indeed, the chemists who will use CoMFA are among the most visually oriented classes of scientists. Thus, in addition to its power, CoMFA is also much more graphically oriented than other 3D-QSAR approaches, in both its input requirements, (molecular models), and its output, (scatter plots and contour maps). Literally, the only number with which the end-user needs L to be concerned is the cross-validated $R^2$, the figure-of-merit for a CoMFA analysis.

It should be evident that due to the manner in which the CoMFA 3D-QSAR methodology is structured, that is, as an attempt to relate differences in biological activity to differences in shape, the commonly shaped areas among the test molecules should not contribute strongly to the solution. Similarly, not all areas of shape difference should be reflected in larger contributions in the solution, but only those areas of shape difference related most strongly to the biological differences. A significant achievement of the present invention is that its solution to the 3D-QSAR interaction energy data table provides a quantitative comparison of molecular shape. Also, because the PLS solution was rotated back into the data set, the determined coefficients have the same units as the data values, and therefore, each term represents its contribution to functionality in the same units from which it was derived, i.e., interaction energies. In general, the larger the magnitude of a coefficient, the more strongly its associated spatial position is related to the observed biological differences. The sign of the coefficient is related to the sign of the effect of the change on the biological difference.

Further, the terms in the solution are uniquely associated with positions in three-dimensional space (lattice coordinates) since the solution preserves the column structure of the data table. Therefore, a graphic plot in three dimensions of the terms values (lattice point by lattice point) results in a display of the regions in space most responsible for predicting changes in molecular functionality.

For comparison and study, several values representative of each term may be displayed for each point:
1) the standard deviation of the column values times the 3D-QSAR coefficient;
2) the 3D-QSAR coefficient only;
3) the standard deviation of the column only;
4) the column value for one of the molecules;
5) the column value for a molecule times the 3D-QSAR coefficient; or
6) any data from an external file.

The values for steric and electrostatic terms may be displayed separately or in combination.

Figure 4A:
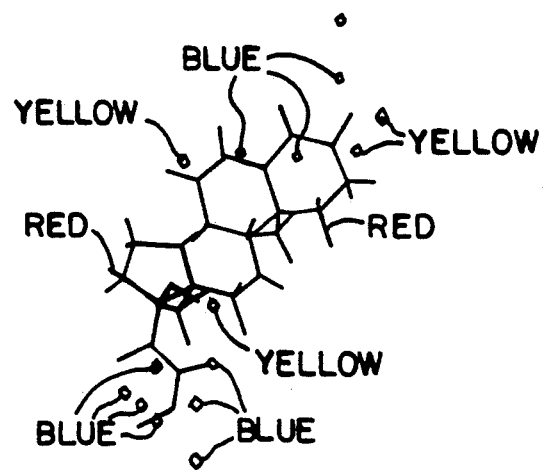
FIG. 4A is the scatter plot of FIG. 3A with a molecule superimposed so that the three-dimensional relationship of the molecule to the CoMFA solution can be seen.

Two methods of graphic presentation are utilized. First the terms can be presented as a three-dimensional scatter plot color coded to represent the magnitude and sign of the association between the energy field change and biological activity at each lattice point. Thus, in FIG. 3A, the blue dots represent solution coefficients whose values indicate that nearby increases in molecular size would increase molecular binding, while the yellow areas indicate that nearby increases in size would decrease molecular binding. The molecular modeling program used originally to place the molecules into the lattice may be used to superimpose any one of the molecules from the data set onto the three-dimensional display so that the colored areas of significance may be more easily identified with specific atomic positions as is shown in FIG. 4A.

Figure 4B:
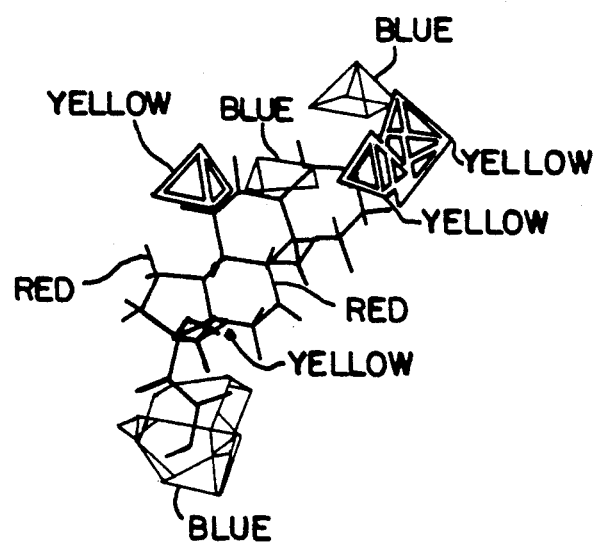
FIG. 4B is the counter plot of FIG. 3B with a molecule superimposed so that the three-dimensional relationship of the molecule to the CoMFA solution can be seen.

The second method of viewing the information is to plot contours in space. The contour lines connect points (terms) in lattice space having similar values. The contours form polyhedra surrounding space where the values are higher or lower than a user selected cutoff value. The colored polyhedra in each map surround all lattice points where CoMFA strongly associates changes in field values with differences in the biological parameter. FIG. 3B shows a contour plot by itself while FIG. 4B shows a contour plot with a molecule from the data set superimposed for study and comparison.

These displays clearly show the user where either increased steric bulk or increased electrostatic interaction in a region is related to greater biological affinity. Conversely, also shown are those areas where increasing steric bulk or increasing electrostatic interaction interfer (negative relate) with biological affinity.

One can view CoMFA maps not only as three-dimensional representations of molecular shapes which are significantly related to biological functionality, but also as maps of the receptor spaces. In this view, the higher interaction areas reflect sterio specific orientation requirements of the receptor. The map of the steric terms gives an indication of the steric requirements of the receptor site, and the map of the electrostatic terms gives an indication of the electrostatic requirements of the receptor site. When combined with chemical knowledge of the receptor site derived by other means, this information can lead to interesting and predictive insights into the nature of the receptor site. This method is clearly distinguished from the prior art, such as the distance geometry method, in that no guess as to specific locations of atoms at the receptor site is needed before the 3D-QSAR is determined. In CoMFA, steric specific and electrostatic specific information about the receptor site is derived from the 3D-QSAR. One caution must be mentioned about over-interpreting the contour coefficient map as a receptor map. In a highly underdetermined system such as is used in CoMFA with many times more coefficients to be evaluated than compounds, a number of 3D-QSAR solutions to the data set may exist equally consistent with any given set of compounds and data. While this does not diminish the predictive ability or solution found by the PLS/cross-validation method, it would suggest some caution be utilized in interpreting the final map as a receptor site map.

Finally, the CoMFA map may be rotated and viewed from any desired angle in order to more thoroughly appreciate the space specific information it contains.

PREDICTIVE POWER

A significant advance achieved by the present invention over the prior art is the ability to quantitatively predict the likely biological behavior of a molecule not included in the initial data set. A major impetus for developing 3D-QSAR to describe intermolecular associations, is that such an understanding should enable the design of molecules with even higher biological affinities than those presently known. One application of this ability would be the design of new and more powerful/selective drugs. In the prior art, to the extent that suggestions as to modified molecular structures could be made based on the results of QSAR analyses, it was necessary to synthesize the suggested molecule and test it in the relevant biological system before knowing whether a desired change had been achieved. By comparison, the present invention allows immediate testing of proposed molecular modifications against the CoMFA model-solution. Thus, based upon the spatial areas shown by CoMFA to be significant to biological activity, a new molecular configuration can be proposed. The proposed molecule can be placed and aligned in the lattice structure, its interaction energies calculated, and those energies entered into a 3D-QSAR equation using the coefficients derived from the original data table. The equation yields a predicted biological value for the molecule.

The calculated interaction energies for the proposed molecule can also be displayed and compared to the initial CoMFA spatial maps. One can immediately see on the resulting display whether the changes made in the molecule design are associated with the same higher interaction energy terms and spatial areas as those predicted from the CoMFA. It has been found that the CoMFA methodology predicts with high accuracy the biological value of proposed molecules in those cases where the molecules have been synthesized/tested or were unknown when the CoMFA analysis was done. Thus, the present invention provides a quantitative process for investigating the structures of unsynthesized molecules to determine their likely biological activity. The importance of this ability to all aspects of medicinal and biological chemistry can hardly be overstated.

In addition, the CoMFA methodology will permit the retrieval of molecules with desired structures from among data bases of molecules whose shapes are described by interaction energies. Indeed, it may be found that unsuspected molecules, never tested in a given biological system, may possess the proper shape to interact as well as or better than the known molecules.

CoMFA results can also direct the user towards determining the actual conformer involved in the molecular interaction. As noted earlier, the final CoMFA display identifies those spatial volumes most highly associated with differences in biological activity. The user may superimpose any of the molecular conformations, either as stick models or in interaction energy form, used in generating the 3D-QSAR table onto the solution display to compare the shape of that conformation to those critical spatial volumes.

To an extent, some correlation must exist since the solution is derived from a table containing all conformations. However, the conformation which comes closest to matching the requirements of the solution space can be used as the principal conformation in generating another 3D-QSAR table. If the predictive $R^2$s for the new table solution are higher than for the first solution, the chosen conformation is more likely to be the active conformation. This procedure may be repeated as many times as the user feels necessary.

It will be possible with the process of the present invention to substantially reduce the trial and error approach to drug design with consequent savings of time, energy, and money. Extensive use of CoMFA should also lead to more rapid development of life-saving drugs. As mentioned earlier, CoMFA can be used as well for other types of intermolecular associations such as studies in antigen antibody binding and changes in the receptor site of genetically altered enzymes. All that is needed is some knowledge of the molecular environment involved such as the X-ray crystal structure of the enzyme and knowledge of how substituted amino acids fit into the X-ray structure. The discussion of the present invention in terms of substrate-enzyme binding affinities should be understood to be representative of the utility of CoMFA as it is appreciated at the moment, but not in any way limiting of the generality of the methodology or process disclosed in this invention. Indeed, the spatial maps generated are such an extraordinarily powerful tool in investigating intermolecular associations that it is believed the full import of the process is yet to be fully realized.

SOFTWARE DISCLOSURE

The present invention is intended to be utilized in conjunction with one of several molecular modeling environments now commercially available. These environments have different hardware and display capabilities, as well as different software modalities available. Typically, however, the computing and display functions equivalent to that found in the Evans and Southerland Series 300 molecular modeling units would be most helpful in practicing the present invention.

Six source code listings are provided: (The source code is available in the filer wrapper, not print herein.) Q3DEF.C, DABDEF.C, EVAL.C, FFIT.C, PLS.FOR, and MAP.C. All source code is in the language except for PLS.FOR which is in Fortran. FFIT.C, EVAL.C, PLS, and MAP.C are programs while Q3DEF.C is a data description all data for which the CoMFA programs look, and DABDEF.C contains the global data structures for software which manages tables of numbers.

Figure 5:
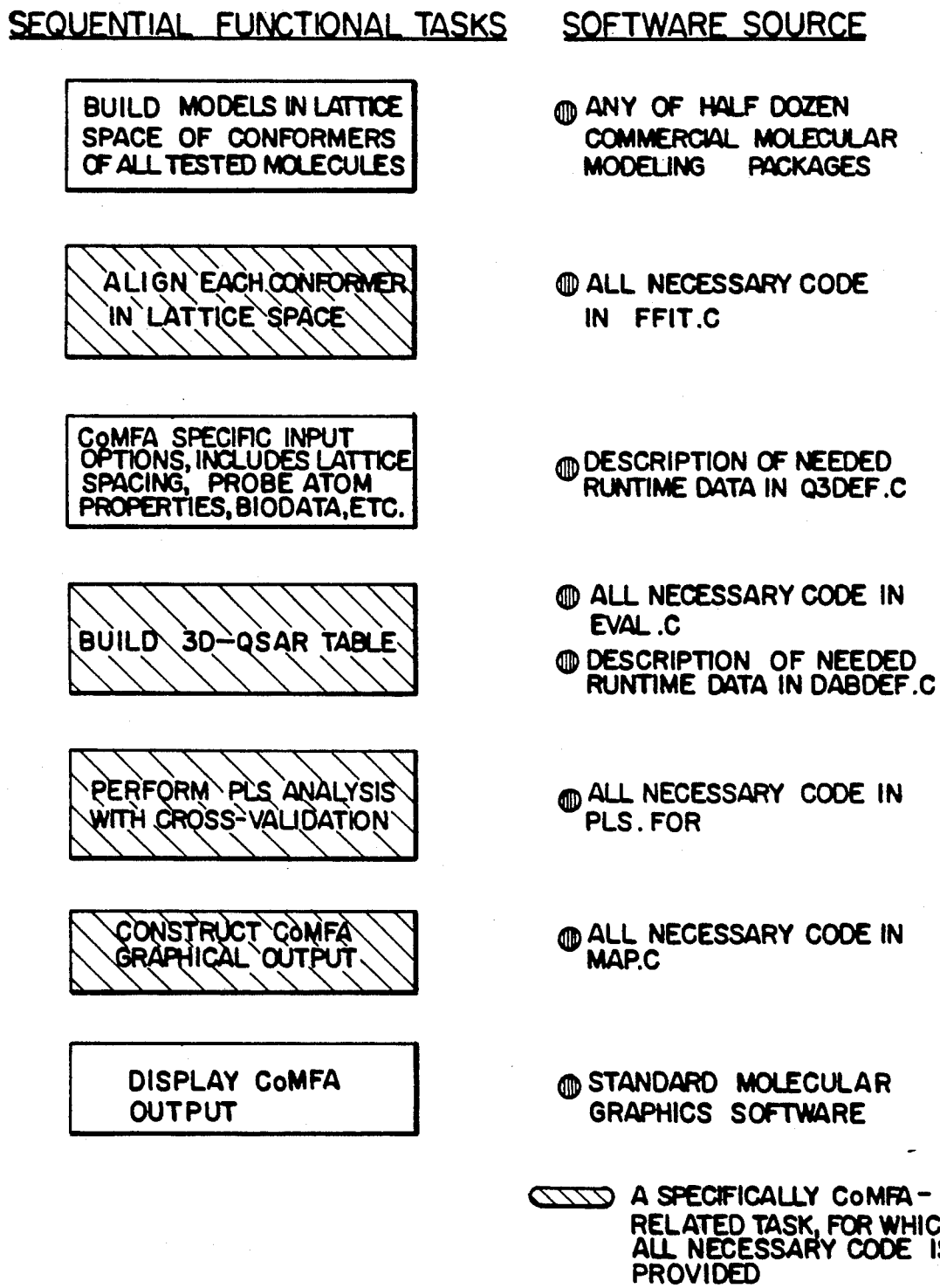
FIG. 5 is a schematic illustration of the integration of the CoMFA software into a standard molecular modeling environment.

FIG. 5 schematically shows how the CoMFA programs are integrated into a standard molecular modeling environment. As mentioned earlier, several programs are commercially available which can be used to build molecules of interest and their conformers into three-dimensional lattice space although the Tripos Associates, Inc. program SYBYL was used by the inventor. Similarly, while the inventor used the Tripos Associates, Inc. program DABYL to manage tables of numbers, functionally equivalent software includes RS/1 from BBN Software in Cambridge, Mass.

The methodology of the present invention provides for selection of input options/parameters by the user. The data structures for the input options/parameters are specified in Q3DEF.C while DABDEF.C specifies data structures for the data management program. EVAL.C creates a 3D-QSAR table from the information provided by the molecular modeling program and from the input of biological parameters. FFIT.C performs the Field Fit alignment procedure to properly align molecules, either conformers or the molecules in the tested series. PLS performs the Partial Least Squares Analysis and cross-validation of the 3D-QSAR table created by EVAL.C. Finally, MAP.C generates the spatial maps for graphic output. If and when it is desired to superimpose a molecular structure on the output maps of the CoMFA methodology, the standard molecular modeling programs can be used to do so.

If commercial programs are not available, or if the user wishes to use programs other than Tripos Associates, Inc.'s, or if the user wishes to develop his own software environment in which to implement CoMFA, a functional description of all subroutines called by the four core CoMFA program segments is included following the source code listings. In actual use all the programs would be compiled and linked before execution. The PLS program ca be converted into a stand alone program by converting appropriate comment lines at the beginning of the program back into source code.

As disclosed in the program listings, the CoMFA programs provide the user with a number of options. A complete list of options is given here:

In FIELD FIT:
1) Calculations may be done either in "interactive" mode progress monitored on terminal or "batch"—separately, with notification of the user when complete.
2) Weighting of lattice points may be either: evenly; by QSAR coefficient; or by user-specified weights.
3) The steric and electrostatic components may either be handled independently or summed together.
4) Overall translations/rotations may be included or excluded.
5) Torsional rotations may be included (if so, user to specify which ones) or excluded.
6) How far should the molecule be moved in a trial move (initially—this value changes as Simplex minimization proceeds)?
7) Convergence criterion—how small must the geometric change in successive steps be before field fit is considered done?
8) Maximum number of steps before field fit quits, regardless of whether convergence has occurred.
9) The template ("target") field may be from a single molecule (conformer) or from several molecules (conformers) averaged together.
10) If in interactive mode (1 above), should the intermediate results be displayed after each 10 steps?
11) If in interactive mode and displaying intermediate results, should the user be asked whether to continue after each display?
12) Is this a regular field fit or else a "docking" field fit (where the objective is to maximize difference by field-fitting to complement of template field)?
13) What should be done to save the result of the field fit? The options are: nothing, write to an external file, replace the molecule in the database.

In EVAL.C:
1) The type of alignment to be performed on the molecule conformers. The options are: none, FIT, ORIENT, field fit.
2) Should the results of alignment be stored back into the database?
3) Should energy be "smoothed" (in which case the QSAR table value at a lattice point will be the average of the actual value and nine other values spaced evenly around that point)?
4) Element/hybridization state of the probe atom (controls its steric or van der Waals properties).
5) Charge of the probe atom (controls its electrostatic effect).
6) Method of estimating van der Waals parameters (standard SYBYL method or calculated by Scott/Scheraga—reference to Scott/Scheraga is in the code itself).
7) Repulsive van der Waals exponent value (usually 12).
8) Electrostatic exponent (usually 2, equivalent to a 1/r dielectric).
9) Maximum steric value to be recorded in the 3D-QSAR table (usually 30 kc/m).
10) Highest energy conformation to consider when representing a molecule as the average of conformations (excessively high energy conformers make vanishingly small contributions to the overall shape).
11) Should a 3D-QSAR table column be excluded if ANY compound in the QSAR table contributes a maximum steric value?
12) Should identities of excluded 3D-QSAR columns (which occur whenever there is no difference in value along a column in the table, because all compounds have a maximum steric value at that lattice point) be listed to terminal?

In PLS.FOR:

1) Is cross-validation to be done? If so, the number of cross-validation groups.

2) Is "bootstrapping" to be done? If so, the number of bootstrapping trials.

3) The number of components to extract.

4) Should data in individual columns be autoscaled (scaled so that the mean of values is 0.0 and the standard deviation is 0.0)? (This particular procedure is not recommended with CoMFA but is included as a general procedure available for use with PLS.)

5) Is there any relative weighting of columns? (When including other properties such as log P, it is necessary to give them extra weight in order to compete with the large number of field descriptor columns.)

6) Convergence criteria, specifically, epsilon, number of iterations, to be used within PLS itself. (A warning message printed if a round of PLS is ended by the number of iterations being exceeded rather than by a difference less than epsilon being obtained.)

In MAP.C:

1) What is the source of the 3-D data to plot, contour, or list? The options are (1) standard deviation of column times QSAR coefficient (2) standard deviation of column only (3) QSAR coefficient only (4) column value for an individual compound (5) column value for an individual compound times QSAR coefficient (6) external file.

2) Which aspect of 3-D data to plot or contour? The choices are steric, electrostatic, or both steric and electrostatic in separate display areas.

While the preceding written description of CoMFA is provided as an aid in understanding CoMFA, it should be understood that the source code listing constitute a complete disclosure of CoMFA.

©1991 Tripos Associates, Inc. All Rights Reserved

Having thus described the invention, what it is desired to claim and thereby protect by Letters Patent is:

1. A computer-based method of generating and visualizing a three-dimensional quantitative structure activity relationship of a series of molecules comprising the steps of:
   (a) defining molecular shape descriptors for each molecule in said series of molecules wherein each molecule is associated with a unique parameter value;
   (b) aligning each molecule in said series with the common shape elements of all the molecules in said series;
   (c) correlating the molecular shape descriptors and unique parameter value of each molecule with all the other molecules in said series;
   (d) visually displaying using computer graphics the correlation among the molecules in said series.

2. The computer-based method of claim 1 wherein the shape of each molecule in Step (a) is defined by a means for calculating the steric and electrostatic interaction energies between a mathematical representation of a probe and the molecule at every intersection point of a lattice surrounding the molecule.

3. The computer-based method of claim 2 wherein in Step (b) each molecule is aligned by minimizing the root mean squared difference in the sum of steric and electrostatic interaction energies averaged across all lattice points between the molecule and the other molecules in the series.

4. The computer-based method of claim 3 wherein the correlation in Step (c) is performed by partial least squares analysis using cross-validation after each component extraction.

5. The computer-based method of claim 4 wherein the correlation among the molecules is visualized in Step (d) by displaying in three dimensions the correlation solution values corresponding to each point in lattice space.

6. A computer implemented methodology for deriving a three dimensional quantitative structure activity relationship (3-D QSAR) among molecules each of which is associated with a measure of activity and whose basic structures, including conformers, have been modeled in a three dimensional lattice comprising the following steps:
   a. selecting a first conformer of a first molecule;
   b. successively placing a mathematical representation of a probe of user specified size and charge at each lattice intersection;
   c. calculating the stearic and electrostatic energies of interaction between the probe and the conformer at each lattice intersection;
   d. entering the stearic and electrostatic interaction energies calculated in step c in a row of a data table identified with the conformer;
   e. selecting a next conformer of the first molecule and repeating steps b and c;
   f. aligning said next conformer to the first conformer;
   g. entering the interaction energies for said next conformer produced by the alignment as the next row in the date table identified with the conformer;
   h. repeating steps e through g for all conformers of the first molecule to be considered;
   i. weighting and then averaged interaction energies in the a row of a 3-D QSAR data table along with the measured activity value associated with the molecule;
   j. repeating steps a through i for all molecules to be considered;
   k. aligning all molecules to said first molecule in the group being considered;
   l. extracting a first component by applying the partial least squares statistical methodology to said 3-D QSAR data table;
   m. performing a cross validation cycle on said 3-D QSAR data table using solution coefficients resulting from the first component extraction;
   n. extracting the next component by applying the partial least squares statistical methodology to said 3-D QSAR data table;
   o. performing a cross validation cycle on said 3-D QSAR data table using coefficient resulting from said next component extraction;
   p. repeating steps n through o until all desired components have been extracted;
   q. adding the extracted components;
   r. rotating the partial least squares solution consisting of the sum of the extracted components back into the original metric space;
   s. driving the solution coefficients; and
   t. displaying the solution.

7. The method of claim 6 further comprising the additional step of varying the size and charge of the probe by varying its mathematical representation in accordance with user specified criteria as it is placed successively at each lattice intersection.

8. The method of claim 6 further comprising the additional step of varying the spacing of the lattice intersections in accordance with user specified criteria as the mathematical representation of the probe is placed successively at each lattice intersection.

9. The method of claim 6 in which the alignment of the conformers is performed by the FIT method.

10. The method of claim 6 in which the alignment of the conformers is performed by the ORIENT method.

11. The method of claim 6 in which the alignment of the conformers is performed by the FIELD FIT method.

12. The method of claim 6 in which the alignment of the molecules is performed by the FIT method.

13. The method of claim 6 in which the alignment of the molecules is performed by the ORIENT method.

14. The method of claim 6 in which the alignment of the molecules is performed by the FIELD FIT method.

15. The method of claim 6 in which the interaction energies of the conformers are weighted before averaging in accordance with a Boltzman distribution over the energies of the conformers.

16. The method of claim 6 further comprising the additional step, before performing the partial least squares analysis, of placing in the columns of each row of a 3-D QSAR data table in addition to the interaction energies additional molecular parameters associated with the molecule represented by the row.

17. The method of claim 6 in which the solution terms are displayed in three dimensional scatter plots corresponding to points in lattice space.

18. The method of claim 17 further comprising the additional step of displaying a molecular model superimposed on the scatter plots.

19. The method of claim 6 in which the solution terms are displayed in three dimensional contour plots defining volumes in lattice space.

20. The method of claim 19 further comprising the additional step of displaying a molecular model superimposed on the contour plots.

21. The computer implemented Field Fit method of aligning molecules according to their shapes where the molecular shape descriptors are the calculated molecular field values of stearic and electrostatic interaction energies between each molecule and a mathematical representation of a probe samples at all points in a three dimensional lattice in which the molecules are modeled, comprising the following steps:
   a. generating interaction energies which represent stearic repulsion beyond the boundary of said three dimensional lattice; and
   b. computing and minimizing the root mean squared difference in the sum of the stearic and electrostatic interaction energies averaged across all lattice points between the molecule to be aligned and a reference molecule with respect to the six rigid-body degrees of freedom.

22. The method of claim 21 in which the minimization is performed by the Simplex method.

23. The method of claim 21 further comprising the additional step of displaying the molecular alignment.

24. The method of claim 21 further comprising the additional step of weighting the contributions to the minimization of those lattice positions which may be particularly significant to alignment of the molecules.

25. The method of claim 24 further comprising the additional step of displaying the effect of various weighting choices on molecular alignment.

26. The method of claim 21 further comprising the additional step of weighting the contributions to the minimization of the field differences and the edge steric repulsion.

27. The method of claim 26 further comprising the additional step of displaying the effect of various weighting choices on molecular alignment.

28. The method of claim 21 further comprising the additional step of minimizing the root mean squared difference in the calculated internal energies between the molecule to be aligned and a reference molecule as the torsion angles and internal geometry of the molecule to be aligned are altered within user defined limits.

29. The method of claim 28 in which the minimization is performed by the Simplex method.

30. The method of claim 28 further comprising the additional step of displaying the molecular alignment.

31. The method of claim 28 further comprising the additional step of weighting the contributions to the minimization of those lattice positions which may be particularly significant to alignment of the molecules.

32. The method of claim 31 further comprising the additional step of displaying the effect of the various weighting choices on molecular alignment.

33. The method of claim 28 further comprising the additional step of weighting the contributions to the minimization of the field differences, the edge steric repulsion, and the differing internal energies as torsion angles and internal geometries are altered.

34. The method of claim 33 further comprising the additional step of displaying the effect of the various weighting choices on molecular alignment.

35. The computer implemented method of aligning or docking shape complementary molecules where the molecular shape descriptors are the calculated molecular field values of stearic and electrostatic interaction energies between each molecule and a mathematical representation of a probe sampled at all points in a three dimensional lattice in which the molecules have been modeled, comprising the following steps:
   a. generating interaction energies which represent stearic repulsion beyond the boundary of said three dimensional lattice; and
   b. computing and maximizing the root mean squared difference in the sum of the stearic and electrostatic interaction energies averaged across all lattice points between the molecule to be aligned and a complementary molecule with respect to the six rigid-body degrees of freedom.

36. The method of claim 35 in which the maximization is performed by the Simplex method.

37. The method of claim 35 further comprising the additional step of displaying the molecular alignment.

38. The method of claim 35 further comprising the additional step of weighting the contributions to the maximization of those lattice positions which may be particularly significant to alignment of the molecules.

39. The method of claim 38 further comprising the additional step of displaying the effect of various weighting choices on molecular alignment.

40. The method of claim 35 further comprising the additional step of weighting the contributions to the maximization of the field differences and the edge steric repulsion.

41. The method of claim 40 further comprising the additional step of displaying the effect of various weighting choices on molecular alignment.

42. The computer implemented method of determining the likely biological or chemical activity of a test molecule whose basic structure has been modeled in a three dimensional lattice by comparing its three dimensional shape to the shape of other molecules of known biological or chemical reactivity whose 3D-QSAR has previously been determined by the COMFA methodology, comprising the following steps:
   a. successively placing a mathematical representation of a probe of user specified size and charge at each lattice intersection;
   b. calculating the steric and electrostatic energies of interaction between the probe and the test molecule at each lattice intersection;
   c. aligning the test molecule to the molecules in the molecular series used to derive the 3-D QSAR solution coefficients; and
   d. applying the solution coefficients derived in the 3-D QSAR COMFA analysis of the molecular series to the interaction energies of the test molecule to predict the biological or chemical parameter value which the test molecule should possess.

43. The method of claim 42 further comprising the additional step of displaying the calculated interaction energies for the test molecule with the previously derived 3-D QSAR solution coefficients in order to visualize for comparison areas of similarity or difference.

44. The method of claim 42 in which the test molecule has not been synthesized and whose structure and that of its conformers is determined for purposes of placement in the three dimensional lattice from molecular modeling considerations or by molecular modeling techniques.

45. The computer implemented method of generating and visualizing a three dimensional structure activity relationship among a group of molecules having related chemical or biological properties comprising the following steps:
   a. generating for each molecule in the group a row in a data table consisting of molecular parameters uniquely associated with each individual molecule;
   b. performing a correlation of all the rows of data in the data table using the partial least squares statistical methodology including cross validation;
   c. rotating the solution back into the original metric space; and
   d. displaying the correlations among the molecules in the group.

46. A computer implemented method for deriving the correlation between molecular descriptors and measured chemical or biological properties of a group of molecules where there are many more molecular descriptors for each molecule in the group than there are number of molecules in the group comprising the following steps:
   a. generating a data table each row of which contains in its columns the molecular descriptors associated with a single molecule of the group as well as the value of the measured chemical or biological property of that molecule;
   b. extracting a first component by applying the partial least squares statistical methodology to the rows of the data table;
   c. performing a cross validation cycle on the data table using solution coefficients resulting from the first component extraction;
   d. extracting the next component by applying the partial least squares statistical methodology to the rows of the data table;
   e. performing a cross validation cycle on the data table using coefficients resulting from said next component extraction;
   f. repeating the steps d and 3 until all desired components have been extracted;
   g. adding the extracted components;
   h. rotating the partial least squares solution consisting of the sum of the extracted components back into the original metric space and deriving the solution coefficients; and
   i. displaying the solution.

47. A system for deriving a three dimensional quantitative structure activity relationship (3-QSAR) among molecules each of which is associated with a measure of activity and whose basic structures, including conformers, have been modeled in a three dimensional lattice comprising:
   a. means for selecting a first conformer of a first molecule;
   b. means for successively placing a mathematical representation of a probe of user specified size and charge at each lattice intersection;
   c. means for calculating the steric and electrostatic energies of interaction between the probe and the conformer at each lattice intersection;
   d. means for entering the steric and electrostatic interaction energies calculated by means c in a row of a data table identified with the conformer;
   e. means for selecting a next conformer of the first molecule and invoking said means b and said means c;
   f. means for aligning said next conformer to the first conformer;
   g. means for entering the interaction energies for said next conformer produced by the alignment as the next row in the data table identified with the conformer;
   h. means for invoking means e through g for all conformers of the first molecule to be considered;
   i. means for weighting and then averaging the interaction energies across all conformers of the first molecule and placing the averaged interaction energies in the first row of a 3-D QSAR data table along with the biological or chemical value associated with the first molecule;
   j. means for invoking means a through i for all molecules to be considered;
   k. means for aligning all molecules to said first molecule in the group being considered;
   l. means for extracting a first component by applying the partial least squares statistical methodology to said 3-D QSAR data table;
   m. means for performing a cross validation cycle on said 3-D QSAR data table using solution coefficients resulting from the first component extraction;
   n. means for extracting the next component by applying the partial least squares statistical methodology to said 3-D QSAR data table;
   o. means for performing a cross validation cycle on said 3-D QSAR data table using coefficients resulting from said next component extraction;
   p. means for invoking means n through o until all desired components have been extracted;
   q. means for adding the extracted components;

r. means for rotating the partial least squares solution consisting of the sum of the extracted components back into the original metric space;

s. means for deriving the solution coefficients; and t. means for displaying the solution.

48. The system of claim 47 further comprising additional means for varying the size and charge of the probe by means for varying its mathematical representation in accordance with user specified criteria as it is placed successively at each lattice intersection.

49. The system of claim 47 further comprising additional means for varying the spacing of the lattice intersections in accordance with user specified criteria as the mathematical representation of the probe is placed successively at each lattice intersection.

50. The system of claim 47 in which the means for aligning the conformers utilizes the FIT method.

51. The system of claim 47 in which the means for aligning the conformers utilizes the ORIENT method.

52. The system of claim 47 in which the means for aligning the conformers utilizes the FIELD FIT system.

53. The system of claim 47 in which the means for aligning the molecules utilizes the FIT method.

54. The system of claim 47 in which the means for aligning the molecules utilizes the ORIENT method.

55. The system of claim 47 in which the means for aligning the molecules utilizes the FIELD FIT system.

56. The system of claim 47 further comprising means for weighting the interaction energies of the conformers before averaging in accordance with a Boltzman distribution over the energies of the conformers.

57. The system of claim 47 further comprising, before invoking the means for applying the partial least squares analysis, additional means for placing in the columns of each row of a 3-D QSAR data table, in addition to the interaction energies, additional molecular parameters associated with the molecular represented by the row.

58. The system of claim 47 in which the means for displaying the solution further comprises means for displaying the solution terms in three dimensional scatter plots corresponding to points in lattice space.

59. The means for displaying the solution of claim 58 further comprising additional means for displaying a molecular model superimposed on the scatter plots.

60. The system of claim 47 in which means for displaying the solution further comprises means for displaying the solution terms in three dimensional contour plots defining volumes in lattice space.

61. The means for displaying the solution of claim 60 further comprising additional means for displaying a molecular model superimposed on the contour plots.

62. The FIELD FIT system of aligning molecules according to their shapes where the molecular shape descriptors are the calculated molecular field values of stearic and electrostatic interaction energies between each molecule and a mathematical representation of a test probe sampled at all points in a three dimensional lattice in which the molecules are modeled, comprising:

a. means for generating interaction energies which represent stearic repulsion beyond the boundary of said three dimensional lattice; and b. means for computing and minimizing the root mean squared difference in the sum of the stearic and electrostatic interaction energies averaged across all lattice points between the molecule to be aligned and a reference molecule with respect to the six rigid-body degrees of freedom.

63. The system of claim 62 in which the means for minimizing utilizes the Simplex method.

64. The system of claim 62 further comprising additional means for displaying the molecular alignment.

65. The system of claim 62 further comprising additional means for weighting the contributions to the minimization of those lattice positions which may be particularly significant to alignment of the molecules.

66. The system of claim 65 further comprising additional means for displaying the effect of various weighting choices on molecular alignment.

67. The system of claim 62 further comprising additional means for weighting the contributions to the minimization of the field differences and the edge steric repulsion.

68. The system of claim 67 further comprising additional means for displaying the effect of various weighting choices on molecular alignment.

69. The system of claim 62 further comprising additional means for minimizing the root mean squared difference in the calculated internal energies between the molecule to be aligned and a reference molecule as the torsion angles and internal geometry of the molecule to be aligned are altered within user defined limits.

70. The system of claim 69 in which the means for minimizing utilizes the Simplex method.

71. The system of claim 69 further comprising additional means for displaying the molecular alignment.

72. The system of claim 69 further comprising additional means for weighting the contributions to the minimization of those lattice positions which may be particularly significant to alignment of the molecules.

73. The system of claim 72 further comprising addition means for displaying the effect of the various weighting choices on molecular alignment.

74. The system of claim 69 further comprising additional means for weighting the contributions to the minimization of the field differences, the edge steric repulsion, and the differing internal energies as torsion angles and internal geometries are altered.

75. The system of claim 74 further comprising additional means for displaying the effect of the various weighting choices on molecular alignment.

76. The system of aligning or docking shape complementary molecules where the molecular shape descriptors are the calculated molecular field values of stearic and electrostatic interaction energies between each molecule and a mathematical representation of a probe samples at all points in a three dimensional lattice in which the molecules have been modeled, comprising:

a. means for generating interaction energies which represent stearic repulsion beyond the boundary of said three dimensional lattice; and b. means for computing and maximizing the root mean squared difference in the sum of the stearic and electrostatic interaction energies averaged across all lattice points between the molecule to be aligned and a complementary molecule with respect to the six rigid-body degrees of freedom.

77. The system of claim 76 in which the means for maximizing utilizes the Simplex method.

78. The system of claim 76 further comprising additional means for displaying the molecular alignment.

79. The system of claim 76 further comprising additional means for weighting the contributions to the maximization of those lattice positions which may be particularly significant to alignment of the molecules.

80. The system of claim 79 further comprising additional means for displaying the effect of various weighting choices on molecular alignment.

81. The system of claim 76 further comprising additional means for weighting the contributions to the maximization of the field differences and the edge steric repulsion.

82. The system of claim 81 further comprising additional means for displaying the effect of various weighting choices on molecular alignment.

83. The system for determining the likely biological or chemical activity of a test molecule whose basic structure has been modeled in a three dimensional lattice by comparing its three dimensional shape to the shape of other molecules of known biological or chemical reactivity whose 3D-QSAR has previously been determined by the COMFA methodology, comprising:
  a. means for successively placing a mathematical representation of a probe at each lattice intersection;
  b. means for calculating the steric and electrostatic energies of interaction between the mathematical representation of the probe and the test molecule at each lattice intersection;
  c. means for aligning the test molecule to the molecules in the molecular series used to derive the 3-D QSAR solution coefficients; and
  d. means for applying the solution coefficients derived in the 3-D QSAR COMFA analysis of the molecular series to the interaction energies of the test molecule to predict the biological or chemical parameter value which the test molecule should possess.

84. The system of claim 83 further comprising additional means for displaying the calculated interaction energies for the test molecule with the previously derived 3-D QSAR solution coefficients in order to visualize for comparison areas of similarity or difference.

85. The system of claim 83 in which the test molecule has not been synthesized and whose structure and that of its conformers is determined for purposes of placement in the three dimensional lattice from molecular modeling considerations or by molecular modeling techniques.

86. The system of generating and visualizing a three dimensional structure activity relationship among a group of molecules having related chemical or biological properties comprising:
  a. means for generating for each molecule in the group a row in a data table consisting of molecular parameters uniquely associated with each individual molecule;
  b. means for performing a correlation of all the rows of data in the data table using the partial least squares statistical methodology including cross validation;
  c. means for rotating the solution back into the original metric space; and
  d. means for displaying the correlations among the molecules in the group.

87. A system for deriving the correlation between molecular descriptors and measured chemical or biological properties of a group of molecules where there are many more molecular descriptors for each molecule in the group than there are number of molecules in the group comprising:
  a. means for generating a data table, each row of which contains in its columns the molecular descriptors associated with a single molecule of the group as well as the value of the measured chemical or biological property of the molecule;
  b. means for extracting a first component by applying the partial least squares statistical methodology to the rows of the data table;
  c. means for performing a cross validation cycle on the data table using solution coefficients resulting from the first component extraction;
  d. means for extracting the next component by applying the partial least squares statistical methodology to the rows of the data table;
  e. means for performing a cross validation cycle on the data table using coefficients resulting from said next component extraction;
  f. means for invoking means d and e until all desired components have been extracted;
  g. means for adding the extracted components;
  h. means for rotating the partial least squares solution consisting of the sum of the extracted components back into the original metric space and deriving the solution coefficients; and
  i. means for displaying the solution.

88. A system for generating and visualizing a three dimensional quantitative structure activity relationship of a series of molecules comprising:
  a. means for defining molecular shape descriptors for each molecule in said series of molecules wherein each molecule is associated with a unique parameter value;
  b. means for aligning each molecule in said series with the common shape elements of all the molecules in said series;
  c. means for correlating the molecular shape descriptors and unique parameter value of each molecule with all the other molecules in said series; and
  d. means for visually displaying using computer graphics the correlation among the molecules in said series.

89. The system of claim 88 wherein the means for defining the shapes further comprises means for calculating the steric and electrostatic interaction energies between a mathematical representation of a probe and the molecule at every intersection point of a lattice surrounding the molecule.

90. The system of claim 89 wherein the means for aligning each molecule further comprises means for minimizing the root mean squared difference in the sum of steric and electrostatic interaction energies averaged across all lattice points between the molecule and the other molecules in the series.

91. The system of claim 90 wherein the means for correlating the shape and unique parameter value further comprises means for performing partial least squares analysis using cross validation after each component extraction.

92. The system of claim 91 wherein the means for visually displaying the correlation further comprises means for displaying in three dimensions the correlation solution values corresponding to each point in lattice space.

93. A computer based method of designing a molecule which will bind to a larger molecule which is known to bind other molecules with measured affinities comprising the following steps:
  a. modeling in a three dimensional lattice the basic structures, including conformers, of molecules known to bind with measured affinities to the larger molecule;
b. selecting a first conformer of a first molecule;
c. successively placing a mathematical representation of a probe of user specified size and charge at each lattice intersection;
d. calculating the steric and electrostatic energies of interaction between the probe and the conformer at each lattice intersection;
e. entering the steric and electrostatic interaction energies calculated in step d in a row of a data table identified with the conformer;
f. selecting a next conformer of the first molecule and repeating steps c and d;
g. aligning said next conformer to the first conformer;
h. entering the interaction energies for said next conformer produced by the alignment as the next row in the data table identified with the conformer;
i. repeating steps f through h for all conformers of the first molecule to be considered;
j. weighting and then averaging the interaction energies across all conformers of the first molecule and placing the averaged interaction energies in the first row of a second data table along with the measured activity value associated with the first molecule;
k. repeating steps b through j for all molecules to be considered;
l. aligning all molecules to said first molecule in the group being considered;
m. extracting a first component by applying the partial least squares statistical methodology to said second data table;
n. performing a cross validation cycle on said second data table using solution coefficients resulting from the first component extraction;
o. extracting the next component by applying the partial least squares statistical methodology to said second data table;
p. performing a cross validation cycle on said second data table using coefficients resulting from said next component extraction;
q. repeating steps o through p until all desired components have been extracted;
r. adding the extracted components;
s. rotating the partial least squares solution consisting of the sum of the extracted components back into the original metric space;
t. deriving the solution coefficients;
u. displaying the solution; and
v. synthesizing a molecule with atoms arranged to occupy or not occupy, as is required, the three dimensional spaces/volumes indicated in the display as being critical to binding of the molecule to the larger molecule.

* * * * *

UNITED STATES PATENT AND TRADEMARK OFFICE
CERTIFICATE OF CORRECTION

PATENT NO. : 5,025,388
DATED : June 18, 1991
INVENTOR(S) : Richard D. Cramer III and Svante B. Wold It is certified that error appears in the above-indentified patent and that said Letters Patent is hereby corrected as shown below:

Column 4, line 63 shows an incorrectly stated variable " $e(r_i)(r_i)$ " at the end of the equation and should be corrected to read as follows:
" $e_{(r_i)}(r_i)$ "

Column 5, line 4 shows an incorrectly stated variable " $e(r_i)$ " relating to the previously stated equation, and should be corrected to read as follows:
" $e_{(r_i)}$ "

Column 7, line 54 the word "counter" should be replaced with the word "contour".

Column 7, line 61 the word "counter" should be replaced with the word "contour".

Column 8, line 6 the word "int" should be replaced with the word "into".

Column 11, line 20 after the word "of" the following text should be inserted: "molecules in the lattice was done with the SYBYL program of".

Column 15, lines 7, 12, 27 and 31 the variable "$R^2$" should be replaced with "$r^2$" on each of those lines.

Column 15, line 67 after the word "needs" the letter "L" should be deleted.

UNITED STATES PATENT AND TRADEMARK OFFICE
CERTIFICATE OF CORRECTION

PATENT NO. : 5,025,388

DATED : June 18, 1991

INVENTOR(S) : Richard D. Cramer III and Svante B. Wold

It is certified that error appears in the above-indentified patent and that said Letters Patent is hereby corrected as shown below:

Column 16, line 1 the variable "$R^2$" should be replaced with "$r^2$".

Column 16, line 41 beginning with the word "QSAR" and line 42 beginning with the word "coefficient" should be on the same line.

Column 18, line 42 the variable "$R^2$" should be replaced with "$r^2$".

Column 19, line 18 after the word "description" insert the word "of".

Column 21, line 9 beginning with the word "deviation" and line 10 beginning with the word "0.0" should be on the same line.

Column 22, lines 21 and 24 the word "stearic" should be replaced with the word "steric" in both instances.

Column 22, line 35 after the word "energies" the following phrase should be inserted: "across all conformers of the first molecule and placing the averaged interaction energies".

Column 22, line 36 the phrase "a row" should be replaced by the phrase "first row".

Column 22, line 37 after the word "the" insert the word "first".

Column 23, line 50 after the word "the" insert the phrase "3-D lattice".

Column 24, lines 36, 42, and 45 the word "stearic" should be replaced with the word "steric".

UNITED STATES PATENT AND TRADEMARK OFFICE
CERTIFICATE OF CORRECTION

PATENT NO. : 5,025,388
DATED : June 18, 1991
INVENTOR(S) : Richard D. Cramer III and Svante B. Wold It is certified that error appears in the above-indentified patent and that said Letters Patent is hereby corrected as shown below:

Column 26, line 7 the number "3" should be replaced by the letter "e".

Column 27, lines 56, 61 and 64 the word "stearic" should be replaced with the word "steric" in each of those instances.

Column 28, lines 33 and 34 the word "addition" should be replaced by the word "additional".

Column 28, lines 46, 52, and 55 the word "stearic" should be replaced by the word "steric".

Column 22, line 32 the word "date" should be replaced by the word "data".

Signed and Sealed this

Twenty-first Day of February, 1995

Attest:

Attesting Officer

BRUCE LEHMAN

Commissioner of Patents and Trademarks